United States Patent [19]

Nakagawa et al.

[11] Patent Number: 4,771,060

[45] Date of Patent: Sep. 13, 1988

[54] NOVEL SKIN-WHITENING AGENT

[75] Inventors: Yoshinori Nakagawa, Souja; Toshiko Suda; Masaaki Hayami, both of Okayama, all of Japan

[73] Assignee: Teikoku Seiyaku Kabushiki Kaisha, Kagawa, Japan

[21] Appl. No.: 901,522

[22] Filed: Aug. 28, 1986

[51] Int. Cl.$^4$ .............................. A61K 31/425
[52] U.S. Cl. ............................................ 514/365
[58] Field of Search ..................... 514/365; 548/202

[56] References Cited

PUBLICATIONS

Chem. Abstr. 103:92628g (1985).
Chem. Abstr. 104:24065s (1986).
Chem. Abstr. 75:36010v (1971).

Primary Examiner—Allen J. Robinson
Assistant Examiner—Freda L. Krosnick
Attorney, Agent, or Firm—Birch, Stewart, Kolasch & Birch

[57] ABSTRACT

A novel skin-whitening composition comprising as an active ingredient a compound of the formula:

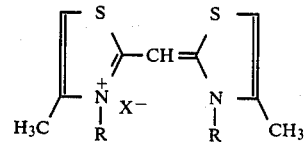

useful for the prophylaxis and treatment of skin troubles due to melanin metabolism disorder.

5 Claims, No Drawings

NOVEL SKIN-WHITENING AGENT

The present invention relates to a novel skin-whitening agent, more particularly, to a skin-whitening composition comprising as an active ingredient a dithiazole-monomethinecyanine compound of the formula:

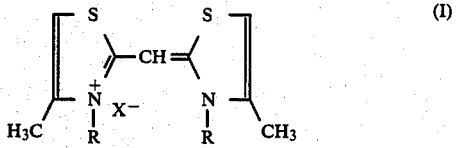

wherein R is an alkyl having 1 to 12 carbon atoms, and X is a halogen atom, or a residue of an acid, in admixture with a conventional pharmaceutical and/or cosmetic carrier, which is useful for the prophylaxis and treatment of skin troubles due to melanin metabolism disorder, for example, dyschromia such as stain (chloasma), freckle, etc.

TECHNICAL BACKGROUND AND PRIOR ART

Generally, human, particularly female, desire to keep skin white. Main detestable skin troubles are stain (chloasma) which increase with ageing and freckle which is more frequently observed in children, and various efforts have been made for preventing and treating these diseases. For such purposes, there have been employed a skin care with rice bran packed in a bag or mud, as well as a treatment of skin with sulfur, salicylic acid or enzymes which have an action peeling horny layers of skin, or vitamin C.

Both stains and freckles are a sort of dyschromia and a pigmentation which grows worse by ultraviolet. In these diseases, particularly in color of skin, melanin pigment participates, and hence, these diseases are usually treated by application of melanin-decomposing agents: bleaching agents (i.e., hydroquinone or derivatives thereof, mercury compounds or peroxides, etc.), by external or oral administration of adrenocortical hormone, or by administration of tyrosinase inhibitors.

However, since such bleaching agents and tyrosinase inhibitors damage original physiological functions of skin and induce undesirable side effects such as leukoderma, dyschromia, contact dermatitis, anemia or hyperthermia, they are not satisfactory. Thus, there is no positively effective method for the treatment of these diseases, but there is rather a passive method employed, such as avoiding sunshine or camouflaging with cosmetics.

OBJECT OF THE INVENTION

In view of the above circumstances, the present inventors extensively investigated as to an improved agent and method for preventing and treating stains and freckles and have found that the dithiazole-monomethinecyanine compounds of the above formula (I) are effective for preventing pigmentation of melanin by applying continuously in a slight amount and are useful for the prophylaxis and treatment of stains and freckles.

An object of the present invention is to provide an improved skin-whitening agent comprising as an active ingredient a dithiazole-monomethinecyanine compound of the formula (I). Another object of the invention is to provide a composition for the prophylaxis and treatment of stains and freckles. A further object of the invention is to provide a method for the prophylaxis and treatment of stains and freckles by administering a skin-whitening agent as set forth above. These and other objects and advantages of the invention will be apparent to skilled person from the following description.

DETAILED DESCRIPTION OF THE INVENTION

The active ingredient in the skin-whitening agent of the present invention is the dithiazole-monomethinecyanine compound of the formula (I) wherein R is a straight chain or branched chain alkyl having 1 to 12 carbon atoms, such as methyl, ethyl, propyl, isopropyl, n-butyl, sec-butyl, tert-butyl, n-pentyl, n-hexyl, n-heptyl, n-octyl, n-decyl, n-undecyl and n-dodecyl; X is a halogen atom such as chlorine, bromine or iodine, or a residue of an acid such as perchloric acid, p-toluenesulfonic acid, nitric acid, nicotinic acid, or orotic acid.

Among the compounds of the present invention, one particularly preferred is a compound of the formula (I) wherein R is n-heptyl and X is iodine, i.e. 4,4'-dimethyl-3,3'-di-n-heptyl-2,2'-monomethinethiazolocyanine iodide [i.e. di-(3-n-heptyl-4-methyl)thiazolylmethine] (hereinafter referred to as "pionine") in view of good absorbability (well balanced hydrophilic and lipophilic properties) and also easier preparation thereof.

It is known that the above preferred compound, pionine has some pharmacological activities such antibacterial activity and an activity for prevention of peroxidation of lipid in biomembrane, and this compound has been used in cosmetics as an antiseptic or antimicrobial agent at a concentration of 20 ppm. However, it has never been known that this compound is remarkably effective for preventing the pigmentation of melanin.

It has newly been found by the present inventors that the compounds of formula (I) are effective for preventing some abnormal melanin conditions, e.g. an abnormal enhancement of melanosome functions due to ultraviolet irradiation and a remarkable activation of tyrosinase, which induce enhanced color of skin, and hence, are useful for preventing dyschromia such as stains and freckles by administering continuously.

In spite of the requirement of a long period of time for the treatment of stains and freckles, the skin-whitening agent containing as an active ingredient the above compounds of the present invention can be used very safely without undesirable side effects which are usually observed in the conventional melanin-bleaching agents, hormones or tyrosinase inhibitors. The active compounds (I) of the present invention can activate skin cells and their metabolism and promote metabolism and excretion of melanin pigment, by which stains and freckles are effectively vanished.

Moreover, the agent of the present invention can exhibit the excellent effect without having an effect on the normal functions of melanosome. This is different from the conventional skin-whitening agents which have a tyrosinase-inhibiting activity or a bleaching activity.

Thus, the skin-whitening agent of the present invention is a new type of medicament.

The whitening agents of the present invention can be administered externally or internally (orally). In the case of an oral administration, the compounds of formula (I) are used in an extremely small amount such as 0.05 to 1 mg in one dosage in adult. In the case of an external administration, the compounds of formula (I) are usually used in a concentration of 0.005 to 0.02% by weight based on the total weight of the external composition. The agents of the present invention are particularly preferably used in a bath. In the case of being used in a bath, the compounds of formula (I) are added to the bath in the small amount of 0.1 to 10.0 mg per 100 liters of water (1-100 μg/l).

An internal and external composition of the present invention can be prepared by conventional methods using conventional pharmaceutically and/or cosmetically acceptable carriers, excipients of diluents. The present compositions may be prepared in any of the conventional preparations, such as granules, tablets and capsules for internal (oral) administration and ointments, plasters, packs and lotions for external use. In the case for a bath, the present compositions can be employed in the form of tablets, powders, granules or solutions, which may also contain other conventional components for bath medicines.

The present invention can be illustrated by the following Preparations, Experiments and Examples.

PREPARATIONS 2,4-Dimethylthiazole (b.p. 146°-147° C.) prepared from monochloroacetone and thioacetamide is reacted with an alkyl iodide at about 170° C. in a solvent to give 3-alkyl-2,4-dimethylthiazolium iodide. To this solution is added an acetic anhydride, and then added dropwise isoamyl nitrite, and the mixture is heated at 110° C. on an oil bath. The resulting crude product is recrystallized from ethanol to provide 4,4'-dimethyl-3,3'-dialkyl-2,2'-monomethine-thiazolocyanine iodide.

The compounds of formula (I) thus prepared are shown in the following Table 1.

TABLE 1

| No. | R | X | m.p. (°C.) |
|---|---|---|---|
| 1 | n-heptyl | iodine | 224-228 |
| 2 | n-heptyl | nicotinic acid residue | 121-124 |
| 3 | n-heptyl | orotic acid residue | 205-209 |
| 4 | ethyl | iodine | 300 |
| 5 | n-dodecyl | iodine | 229-230 |

EXPERIMENT 1

Preventive effect on surface melanism in yellow goldfish:

Method:

Ryukins [a kind of goldfish (weighing 3-5 g, one group: 5 fish)] were fed in water containing 1 μg/l or 10 μg/l of pionine (No. 1 compound in the above Preparations) for 20 days. The goldfish were then transferred into a water bath filled with water containing 0.9% by weight of NaCl in order to induce melanism and fed for 12 days. As a control group, the fish were fed likewise except no active compound was used. The extent of surface melanism and the activity of tyrosinase in the group administered with pionine were compared with those of the control group.

Results:

(i) Effects on surface melanism:

In the control group, surface melanism started on 7th day and were observed in all five goldfish (100%) on 12th day. In the pionine-administered groups, the surface melanism was observed in two of five fish (40%) administered with 1 μg/l of pionine and none of the fish administered with 10 μg/l of pionene. Thus, surface melanism was prevented by administration of the compound of this invention, while the degree of effect varied somewhat depending on the dosage.

(ii) Determination of tyrosinase activity:

As samples to be tested, scales were picked from goldfish of each of groups on 12th day. The samples were each homogenized with 1M phosphate buffer (pH 6.8) and centrifuged. As to the supernatant, tyrosinase was determined by a colorimetry according to the procedure of N. H. Horowitz and Pomerantz (cf. Method in Enzymology, XVIIA, 615-626).

As a result, ΔOD at 475 nm/mg protein/30 min was 0.06 in the control group, 0.05 in the group administered with 1 μg/l of pionine and 0.02 in the group administered with 10 μg/l of pionine. Thus, the tyrosinase inhibitory activity was observed in the group to which pionine was administered.

EXPERIMENT 2

Therapeutic effect on surface melanism in yellow goldfish:

Method:

Ryukins (weighing 3-5 g) were fed in a 0.9% NaCl aqueous solution for 12 days to induce surface melanism. The goldfish were grouped into five fish each. In two experiment groups, the fish were fed in a water bath for 12 weeks, during which pionine was add in an amount of 1 μg/l and 10 μg/l, respectively, three times per week. In the control group, the fish were fed in pure water. The recovery from surface melanism of the experiment groups was compared with that of control group.

Results:

The recovery from surface melanism was not observed in all of the groups within the period of three weeks, but there appeared to be some difference between the experiment groups and the control group after 6 weeks. After 12 weeks, the gold fish returned to their original yellow surface color in 0/10 goldfish (0%) in the control group, 4/10 (40%) in the 1 μg/l pionine-administered group and 8/10 (80%) in the 10 μg/l pionine-administered group.

EXPERIMENT 3

Action in normal black-goldfish:

Black popeyed goldfish (each group: 5 fish) were fed in a water bath. In experimental group, pionine was added to the water bath in a concentration of 10 μg/l, three times per week. In the control group, no pionine was added. After 12 weeks, blackness was retained in both groups and no differences were observed.

EXPERIMENT 4

Effect on tyrosinase activity:

The direct effect of pionine to tyrosinase activity was studied. 0.1 ml of a solution of pionine having various concentrations was mixed with 0.1 ml of 290 unit/ml solution of tyrosinase derived from mushroom (Sigma). To the solution 0.8 ml of 1 mg/ml L-DOPA was added as a substrate, and the resulting solution was incubated for 10 minutes, and then tyrosinase activity thereof was determined.

As a result, the values of ΔOD (at 475 nm) as shown in the following Table 2 were obtained. As is clear from the results, it was found that the addition of $5\times10^{-2}$ to $10^{-5}$% of pionine did not affect on the tyrosinase activity.

TABLE 2

| concentration of pionine (%) | ΔOD (at 475 nm) | | |
|---|---|---|---|
| | 2 min. | 5 min. | 10 min. |
| control | 0.250 | 0.540 | 0.782 |
| $5 \times 10^{-2}$ | 0.248 | 0.540 | 0.786 |
| $5 \times 10^{-3}$ | 0.252 | 0.544 | 0.780 |
| $5 \times 10^{-4}$ | 0.252 | 0.540 | 0.784 |
| $5 \times 10^{-5}$ | 0.250 | 0.538 | 0.780 |

As stated above, it was found that pionine has no tyrosinase inhibitory activity. It was also found that pionine does not affect on the normal metabolism of melanin, but has activity for preventing and treating pigmentation by normalizing the formation, metabolism and excretion of melanin when the subject is in an abnormal condition, for example, in stress.

EXPERIMENT 5

Toxity:

After ten yellow goldfish were fed in water containing 5 mg/l of pionine (500-fold of dosage level for therapeutic purposes) for three days, no fish was died and no abnormality was observed.

EXPERIMENT 6

Acute toxity:

A suspension of pionine in a 0.5% sodium carboxymethylcellulose solution was orally administered to Wistar rats (weighing about 130 g, one group: ten animal) with a stomach sonde. The number of dead rats were counted for 7 days, and $LD_{50}$(g/kg) was calculated by van der Werden's method. As a results, the $LD_{50}$ was 0.47 g/kg in male rats and 0.50 g/kg in female rats. Thus, it is clear that pionine is a compound having an extremely wide safety range, taking into account the above experimental results that it is effective in a concentration of 10 μg/l for preventing and treating melanism of goldfish.

EXPERIMENT 7

Clinical test:

A hundred μg of pionine was orally administered to each of three patients having stains (chloasma) and each of three patients having pigmentations induced by inflammation, once a day when the patients were hungry. This test was continued for 6 months. The effect of pionine was evaluated and classified into four classes by the degree of color as follows:

−1: deepened, 0: not changed, +1: faded, +2: completely disappeared.

The results are shown in Table 3. Evaluation by the patients themselves is also mentioned therein. Meanwhile, a patch test as to known cosmetics which were used by the patients was made for all patients before the clinical test, and if the result was positive (i.e. the known cosmetics are effective on the pigmentation), the use of the cosmetics was prohibited.

As is shown in Table 3, the positive effect was observed in 83% (5/6) of the patients and no side effect was observed in all patients.

TABLE 3

| Run No. | Age of patient | Disease | Effects of pionine | | Patch test | Side effect |
|---|---|---|---|---|---|---|
| | | | Findings on skin | Evaluation by patients | | |
| 1 | 41 | Chloasma | +2 (at 4th month) | effective | − | No |
| 2 | 44 | Chloasma | 0 (at 6th month) | not effective | − | " |
| 3 | 47 | Chloasma | +2 (at 5th month) | effective | − | " |
| 4 | 28 | Pigmentation after inflammation | +2 (at 3rd month) | " | − | " |
| 5 | 42 | Pigmentation after inflammation | +2 (at 5th month) | " | +* | " |
| 6 | 55 | Pigmentation after inflammation | +1 (at 3rd month) | " | − | " |

*Isosafrol was found as a sensitizer.

As described above, the compounds of formula (I) have an excellent therapeutic effect even in an extremely low dosage level and can be continuously administered free from undesirable side effect because of their low toxity. Therefore, they are useful for preventing and treating stains and freckles.

EXAMPLE 1

Tablets are prepared in the following formulation by a usual method.

| Ingredient | mg/tablet |
|---|---|
| Pionine | 0.10 |
| Lactose | 79.90 |
| Corn starch | 62.50 |
| Sucrose fatty acid ester | 7.50 |
| totally | 150.00 |

The tablets were administered to six patients having stains or pigmentations after inflammation, once a day when the patients were hungry, over a 3–6 month period and their positive effects were observed in five of six patients.

EXAMPLE 2

Capsules are prepared in the following formulation by a usual method.

| Ingredient | mg/capsule |
|---|---|
| Compound No. 2 | 0.05 |
| Lactose | 146.95 |
| Sucrose fatty acid ester | 3.00 |
| totally | 150.00 |

The capsules were administered to a patient having stains (34 year old woman), once a day when she was hungry. After three months, the stains on her face had faded.

EXAMPLE 3

Ointments are prepared in the following formulation by a usual method.

| Ingredient | g/100 g |
|---|---|
| Pionine | 0.02 |
| Vaseline ® Petrolatum | 50.00 |
| Vegetable wax | 10.00 |
| Lanolin | 10.00 |
| Sesame oil | 20.00 |
| Glycerin | 10.00 |
| Peppermint oil | q.v. |
| Camphor oil | q.v. |

EXAMPLE 4

Packing agents are prepared in the following formulation by a usual method.

| Ingredient | g /100 g |
|---|---|
| Compound No. 3 | 0.01 |
| Squalene | 1.50 |
| Polyoxyethylene-hardened castor oil (60 E.O.) | 0.50 |
| Glycerin | 4.00 |
| Polyvinylalcohol | 15.00 |
| Ethanol | 10.00 |
| Purified water | totally to 100.00 |

The agent was given, once per two days, to a woman (24 years old) sunburned by a sea bathing. After two weeks, the sunburn disappeared from her face and formation of stains were prevented.

EXAMPLE 5

Bath medicines are prepared in the following formulation.

| Ingredient | Amount |
|---|---|
| Compound No. 4 | 0.04 g |
| Ethanol | 80 ml |
| Purified water | totally to 100 ml |

The agent was employed, once a day, for a woman (27 years old) sunburned by a sea bathing. The agent was used in an amount of 5 ml to 100 liter of water. After two weeks, the observation of her back indicated that there were no formation of new stains.

EXAMPLE 6

Bath medicines are prepared in the following formulation.

| Ingredient | Amount |
|---|---|
| Compound No. 5 | 0.04 g |
| Ethanol | 80 ml |
| Purified water | totally to 100 ml |

The agent was employed on a woman (32 years old) having pigmentations after inflammation. Wetting her face with a towel impregnated with the agent resulted in a fading of the stains after 3-4 months.

EXAMPLE 7

Plasters are prepared in the following formulation.

| Ingredient | Amount | |
|---|---|---|
| Pionine | 0.02 | part by weight |
| Gelatin | 3.00 | part by weight |
| Propyl parahydroxybenzoate | 0.10 | part by weight |
| EDTA | 0.10 | part by weight |
| Polyacrylic acid | 35.00 | part by weight |
| Sodium polyacrylate | 4.00 | part by weight |
| Carboxymethyl cellulose | 3.00 | part by weight |
| d-Sorbitol | 20.00 | part by weight |
| Glycerin | 15.00 | part by weight |
| Purified water | 19.78 | part by weight |
| Flavor | q.v. | |
| totally | 100.00 | |

EXAMPLE 8

Plasters are prepared in the following formulation.

| Ingredient | Amount | |
|---|---|---|
| Pionine | 0.02 | part by weight |
| PVA | 8.00 | part by weight |
| Polyacrylic acid | 1.00 | part by weight |
| Glycerin | 20.00 | part by weight |
| Isopropyl myristate | 10.00 | part by weight |
| Surfactant | 2.00 | part by weight |
| Triethanolamine | 8.00 | part by weight |
| Purified water | 50.98 | part by weight |
| Flavor | q.v. | |
| totally | 100.00 | |

We claim:

1. A method for the treatment of dyschromia, which comprises administering to a patient in need of said treatment an effective amount for the treatment of dyschromia of a skin-whitening composition comprising an effective skin-whitening amount of an active compound ingredient having the formula:

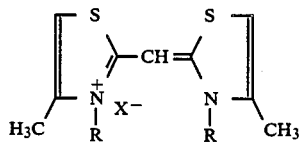

wherein R is an alkyl having 1 to 12 carbon atoms and X is a halogen atom or a residue iof perchloric acid, p-toluenesulfonic acid, nitric acid, nicotinic acid or orotic acid, in admixture with a pharmaceutically acceptable carrier.

2. The method of claim 1, wherein the composition is administered externally.

3. The method of claim 2, wherein the composition comprises 0.005 to 0.02% by weight of the ingredient based on the total weight of said composition.

4. The method of claim 1, wherein the composition is administered internally.

5. The method of claim 4, wherein the composition comprises 0.05 to 1 mg in one dosage in an adult.

* * * * *